United States Patent [19]
Abele et al.

[11] Patent Number: 5,693,014
[45] Date of Patent: Dec. 2, 1997

[54] BALLOON CATHETER

[75] Inventors: John E. Abele, Concord; Ronald A. Sahatjian, Lexington, both of Mass.

[73] Assignee: Boston Scientific Corporation, Natick, Mass.

[21] Appl. No.: 441,603

[22] Filed: May 15, 1995

Related U.S. Application Data

[63] Continuation of Ser. No. 110,655, Aug. 23, 1993, abandoned.

[51] Int. Cl.⁶ .................................................. A61M 29/00
[52] U.S. Cl. .......................... 604/96; 604/265; 606/194
[58] Field of Search ........................... 604/96, 101–103, 604/172, 265, 280; 606/191–198; 128/207.15, DIG. 14, DIG. 21, 749, 756, 757, 759, 760, 769

[56] References Cited

U.S. PATENT DOCUMENTS

| | | | |
|---|---|---|---|
| 2,701,559 | 5/1955 | Cooper | 128/756 |
| 2,927,584 | 3/1960 | Wallace | 604/96 |
| 3,967,728 | 7/1976 | Gordon et al. | 604/172 |
| 4,447,227 | 5/1984 | Kotsanis | 604/95 |
| 4,465,072 | 8/1984 | Taheri | 604/96 |
| 4,555,242 | 11/1985 | Saudagar | 604/96 |
| 4,572,186 | 2/1986 | Gould et al. . | |
| 4,629,459 | 12/1986 | Ionescu et al. | 623/2 |
| 4,796,629 | 1/1989 | Grayzel . | |
| 4,810,543 | 3/1989 | Gould et al. . | |
| 4,878,906 | 11/1989 | Lindemann et al. | 623/1 |
| 4,896,669 | 1/1990 | Bhate et al | 606/194 |
| 4,917,088 | 4/1990 | Crittenden | 604/96 |
| 4,921,484 | 5/1990 | Hillstead | 604/104 |
| 4,927,412 | 5/1990 | Menasche . | |
| 4,941,877 | 7/1990 | Montano, Jr. | 604/96 |
| 4,950,227 | 8/1990 | Savin et al. | 604/8 |
| 4,955,859 | 9/1990 | Zilber | 604/8 |
| 4,986,830 | 1/1991 | Owens et al. | 606/194 |
| 5,002,531 | 3/1991 | Bonzel | 604/96 |
| 5,019,042 | 5/1991 | Sahota | 604/101 |
| 5,026,377 | 6/1991 | Burton et al. | 606/108 |
| 5,026,607 | 6/1991 | Kiezulas . | |
| 5,049,131 | 9/1991 | Deuss | 604/265 |
| 5,089,005 | 2/1992 | Harada | 606/194 |
| 5,091,205 | 2/1992 | Fan . | |
| 5,092,348 | 3/1992 | Dubrul et al. . | |
| 5,092,877 | 3/1992 | Pinchuk | 623/1 |
| 5,102,402 | 4/1992 | Dror et al. . | |
| 5,232,444 | 8/1993 | Just et al. | 604/96 |
| 5,250,070 | 10/1993 | Parodi | 604/96 |
| 5,320,634 | 6/1994 | Vigil et al. | 606/191 |

FOREIGN PATENT DOCUMENTS 892980  4/1962  United Kingdom .

OTHER PUBLICATIONS

Boston Scientific Corporation, Slider™Thin–Shaft PTCA System brochure, Sep. 1990.

*Primary Examiner*—Mark Bockelman
*Assistant Examiner*—Ronald K. Stright, Jr.
*Attorney, Agent, or Firm*—Pearson & Pearson

[57] ABSTRACT

An expansible balloon catheter has at least a first exterior surface with a given coefficient of friction and a second exterior surface with a greater coefficient of friction. In a compact form only the first exterior surface is exposed to produce a low coefficient of friction during transfer of the collapsed or uninflated balloon to and across a lesion. When inflated, the second surface dominates the first surface and produces an increased coefficient of friction overall thereby to stabilize the balloon in the lesion.

17 Claims, 3 Drawing Sheets

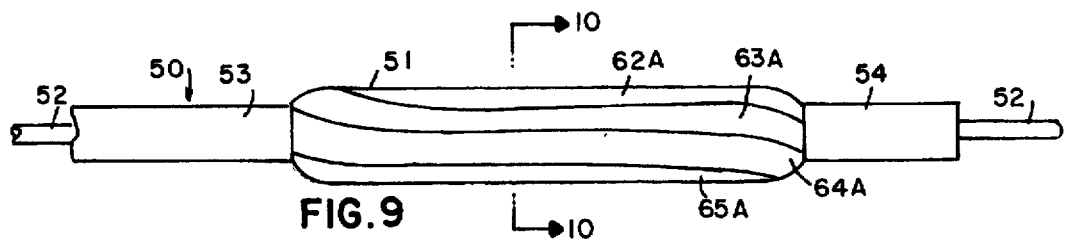
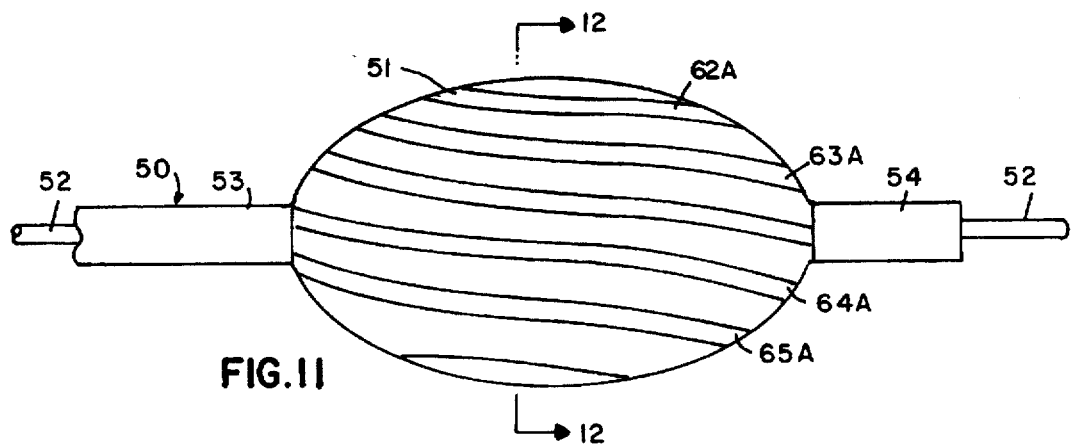
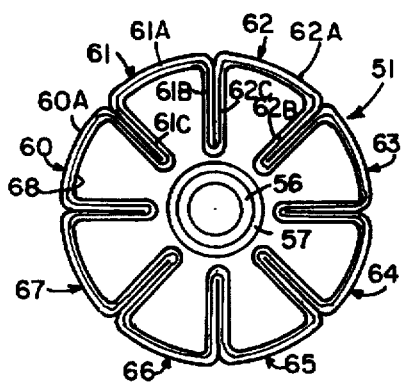
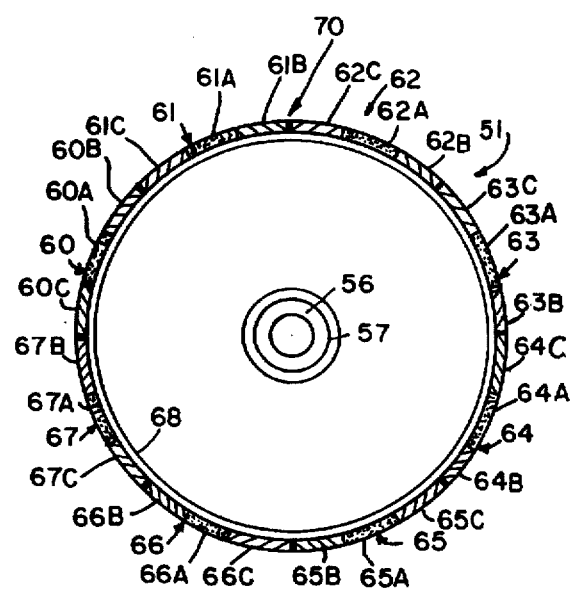

BALLOON CATHETER

This application is a Continuation of Ser. No. 08/110,655 filed on Aug. 23, 1993, now abandoned.

BACKGROUND OF THE INVENTION

1. Field of the Invention

This invention generally relates to balloon catheters and more particularly to the structure of and method of manufacture of balloon catheters.

2. Description of Related Art

Coronary balloon angioplasty involves the steps of inserting a deflated balloon into a coronary artery, advancing the balloon across a lesion until the balloon is centered at the lesion and then inflating the balloon to dilate and remove the stenosis. Significant efforts have been directed toward constructing balloons with smaller cross sections so that they can better cross a tight lesion. However, experience with these smaller balloon catheters has highlighted two desirable, but until now antithetical, characteristics. First, the balloon should exhibit very low coefficient of sliding friction to facilitate initial positioning with minimal trauma. Secondly the balloon should exhibit longitudinal or axial stability during and after inflation. This stability is needed to overcome any tendency for forces exerted by the adjacent tissue to displace or shift the balloon longitudinally in the vessel. Independent efforts have been undertaken to address the issues of sliding friction and of positional stability. However, no activities seem to have been directed toward the development of a balloon that incorporates both characteristics in a single device.

For example, Boston Scientific Corporation, the assignee of this invention, manufactures a Slider™ PTCA Catheter having a lubricous, bonded coating covering the exterior of the balloon. This facilitates access to a lesion and enhances the ability of the balloon to cross the lesion.

Similarly the following patents disclose other coatings adapted for use with balloon catheters:

U.S. Pat. No. 4,810,543 (1989) Gould et al.
U.S. Pat. No. 5,026,607 (1991) Kiezulas
U.S. Pat. No. 5,102,402 (1992) Dror et al.

U.S. Pat. No. 4,810,543 to Gould et al. discloses articles having low friction surfaces and processes for producing such articles. Specifically the Gould et al. patent proposes treating a surface with a mixture of concentrated sulfuric acid and a low molecular weight polyhydroxy compound and removing any excess treating mixture.

U.S. Pat. No. 5,026,607 to Kiezulas discloses a method in which a protective compound, such as urethane, is coupled with a slip additive, such as siloxane and, optionally, a crosslinking agent for a protective compound such as a polyfunctional aziridine, coats the surface of medical apparatus. After setting, the material provides a lubricous surface that is tough and flexible and particularly adapted for use with balloon catheters.

U.S. Pat. No. 5,102,420 to Dror et al. discloses a balloon catheter with an exterior coating of body effecting chemicals. In some embodiments a balloon is inflated, dusted with microcapsules containing a drug and then deflated prior to entry into the patient. Alternately, cusps, folds and other corrugations are formed when the balloon is deflated and capture microcapsules containing the drug material. These microcapsules are then presented when the balloon is inflated.

Each of the Gould et al. and Kiezulas patents discloses methods and procedures for making a device more lubricous. However, none describes any method or procedure for improving axial stability.

The following patents describe balloons that incorporate stabilizing structures to enhance the positioning, engagement and retention of a balloon at a lesion:

U.S. Pat. No. 4,447,227 (1984) Kotsanis
U.S. Pat. No. 4,896,669 (1990) Bhate et al.
U.S. Pat. No. 4,921,484 (1990) Hillstead
U.S. Pat. No. 4,927,412 (1990) Menasche
U.S. Pat. No. 4,986,830 (1991) Owens et al.
U.S. Pat. No. 5,002,531 (1991) Bonzel U.S. Pat. No. 4,447,227 to Kotsanis discloses multipurpose medical devices. Each device has a stabilizing structure for enhancing positioning, engagement and retention of the balloon in a desired lumen. The stabilizing structure is in the form of an additional medical grade balloon or one or more vacuum responsive members, such as active or passive microsuckers.

U.S. Pat. No. 4,896,669 to Bhate et al. discloses a dilation catheter with an outer tubular balloon portion. This balloon portion has circumferential crimps at each of two end transitions and an intermediate axially extended portion with longitudinal crimps. The balloon portion expands readily to a predetermined diameter while undergoing little change in length. Stability of the balloon portion upon and during inflation is substantially achieved, because the transition portions are capable of longitudinal extension in response to minor longitudinal contraction at the two ends of the balloon portion to reduce axial movement when the balloon portion is inflated. This characteristic is stated to reduce axial movement when the balloon is inflated.

U.S. Pat. No. 4,921,484 to Hillstead discloses a mesh balloon catheter device, analogous to an expandable stent, in which the catheter has a distal end with a tube of woven interlaced filaments forming a tubular mesh. The proximal end of the mesh can be moved toward the distal end of the mesh to expand the mesh into surrounding tissue. This particular structure is designed for location in a bladder where the mesh holds the catheter in place while allowing an obstructed fluid flow.

U.S. Pat. No. 4,927,412 to Menasche discloses a catheter adapted for use in a coronary sinus where the sinus walls are slippery, extensible and tapered in a distal direction. Prior catheters normally were subject to axial displacement while being inflated. In accordance with this patent a balloon has a truncated conical surface with outwardly facing, spaced apart, parallel concentric lands for frictionally engaging the coronary sinus. This structure is stated to provide a high retentive force for stabilizing the catheter and preventing its ejection from the coronary sinus.

U.S. Pat. No. 4,986,830 to Owens et al. discloses a valvuloplasty catheter with a balloon that remains positionally stable during inflation. Stability is achieved by providing first and second inflation ports of differing sizes so that the expanding member inflates to create a dog-bone effect that allows the balloon to surround and stabilize the expander member relative to the valve being treated.

U.S. Pat. No. 5,002,531 to Bonzel discloses an inflatable balloon with a hose-like outer skin to which is connected at axially oriented edges and an inner skin also having a hose-like shape. The outer skin acts as a holding membrane. In this particular structure, the inner skin is elastic and undergoes a considerable reduction in diameter when the balloon is deflated. This eases passage of the catheter as it is advances through or retracts from an artery.

Each of the foregoing references therefore proposes some structure for improving axial stability during inflation.

Although the Bonzel patent recognizes a need for easing passage through a lesion, neither it nor any other of these references describe any method or procedure for making a balloon more lubricous. Consequently the prior art defined by these references can be characterized as providing either reduced friction when a balloon is deflated or increased friction when a balloon is expanded, but not both.

SUMMARY

Therefore it is an object of this invention to provide an improved balloon that facilitates placement at a lesion and yet retains its position at the lesion during inflation.

Still another object of this invention is to provide an improved balloon catheter that exhibits different frictional characteristics in its inflated and noninflated states.

Yet another object of this invention is to provide a balloon catheter that has a low coefficient of sliding friction in a deflated state and a higher coefficient of friction in a inflated state.

In accordance with this invention, an expansible balloon has first and second external surface areas having different coefficients of friction. In its compacted form, the surface areas with the higher coefficient friction fold onto each other so the exposed surface areas are formed by the areas with the lower coefficient of friction. When inflated both surface portions engage surrounding tissue.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 9 depicts the application of this invention to an alternative form of a balloon catheter and is a front plan view of the balloon catheter in an uninflated or compact state;

FIG. 10 is a section taken along lines 10—10 in FIG. 9;

FIG. 11 is a front plan view of the balloon catheter in FIG. 9 in an inflated or expanded state; and FIG. 12 is a section taken along lines 12—12 in FIG. 10.

DESCRIPTION OF ILLUSTRATIVE EMBODIMENTS

Figure 1:
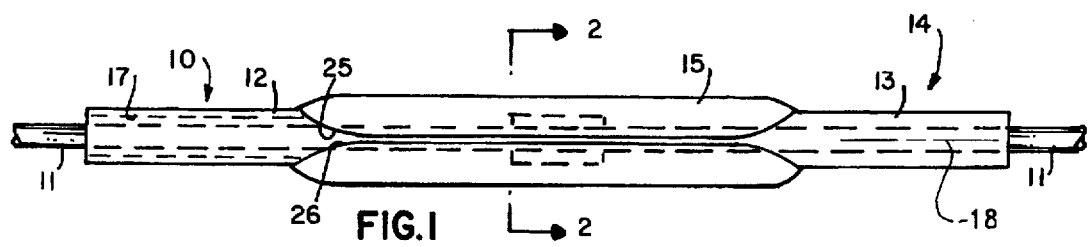
FIG. 1 is a front plan view of a portion of a balloon catheter constructed in accordance with this invention in an uninflated or compact state.

In the embodiment of FIGS. 1 through 4, a catheter 10 slides over a guidewire 11 and includes tubular portions 12 and 13 at a distal end 14 of the catheter 10. A balloon 15 lies longitudinally between and attaches to the tubular portions 12 and 13. Ports 16, shown in phantom in FIG. 3, allow fluid to be admitted to the area of the balloon 15 for expansion. The fluid is supplied either through a lumen 17, in FIG. 1 that carries the guidewire 11 or through an auxiliary lumen (not shown), all is well known in the art.

Figure 2:
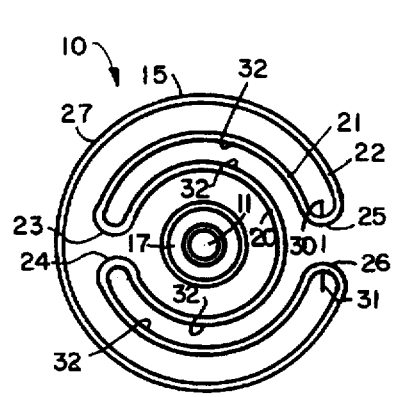
FIG. 2 is a cross-section taken along lines 2—2 in FIG. 1.

FIGS. 1 and 2 depict the disposition of thin balloon material about the catheter 10 and an axis 18 in a compact position. For clarity, FIG. 2 depicts the material out of scale in spaced adjacent layers. In an actual balloon the layers would be tightly packed. The balloon 15 is formed in three concentric layers including an inside layer 20, and intermediate layer 21 and an outer layer 22. The intermediate layer 21 folds back over the inside layer 22 such that the folds 23 and 24 are circumferentially adjacent on the back side of the balloon 15. The intermediate layer 21 and outer layer 22 produce adjacent folds 25 and 26 as shown in FIGS. 1 and 2.

In accordance with this invention, a first integral exterior surface portion, or surface 27, of the outer layer 22 between points marked by the intersection of the axes 30 and 31 with the folds 25 and 26, respectively, is treated to have a first coefficient of sliding that facilitates transferring the balloon 15 across a lesion. The second or remaining integral exterior surface portion, or surface 32, angularly displaced from the first exterior surface 27, has a greater coefficient of sliding friction. As will be apparent, the second surface 32 also has a greater surface area than the first surface 27.

Figure 3:
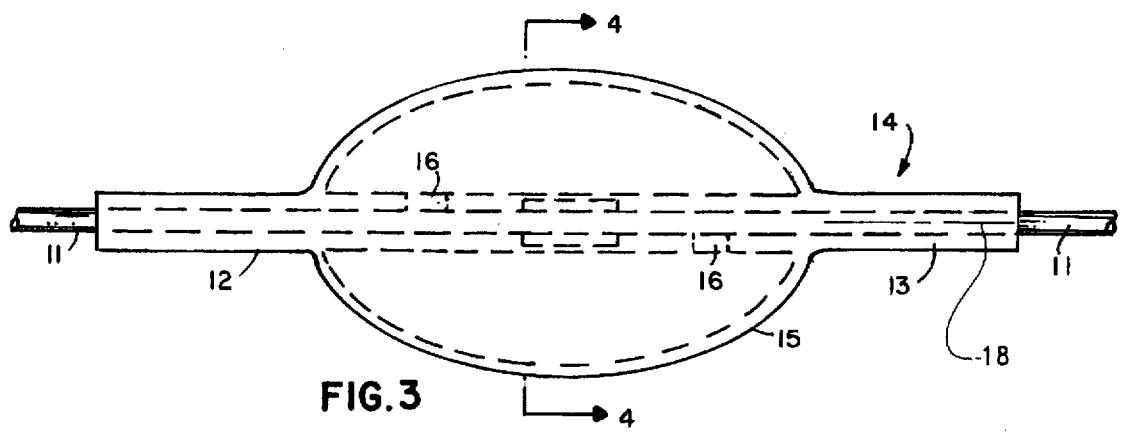
FIG. 3 is a front plan view of the balloon catheter, in FIG. 1 in an inflated or expanded state.
Figure 4:
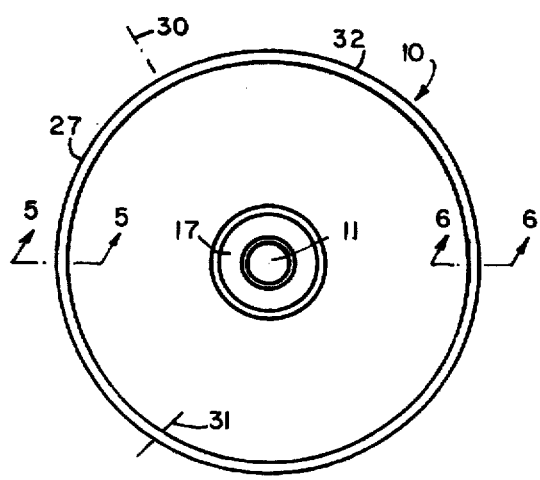
FIG. 4 is a cross-section taken generally along lines 4—4 in FIG. 3.

When the balloon 15 expands to the configuration shown in FIGS. 3 and 4, all of the exterior surfaces 27 and 32 are exposed. However, the second surface 32 with its greater coefficient of friction and greater area dominates, so it increases the overall coefficient of friction for the expanded balloon 15 and is substantially determinative of the overall friction exerted by the balloon 15 against any adjacent vessels. Thus the coefficient of friction for the entire balloon 15 in its expanded form is greater than the coefficient in the collapsed or compact form. Consequently, the balloon 15 exhibits different coefficients of friction in its compacted and expanded forms. If the exterior surface 27 is treated to reduce its coefficient of friction, the balloon 15 has a low coefficient of sliding friction in its compact form that facilitates its placement at a lesion. As the balloon 15 expands, its overall coefficient of friction increases as the surface 32 is exposed, so the balloon 15 retains its position with a patient's vessel during and after inflation.

Figure 5:
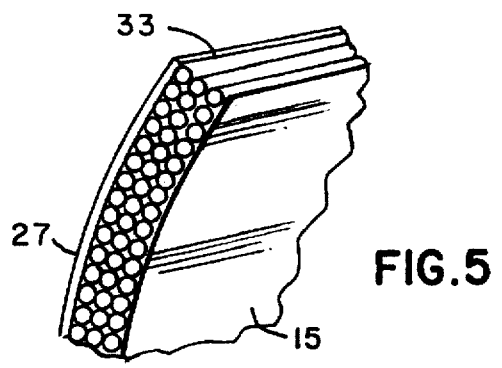
FIG. 5 is an enlarged cross-section taken along lines 5—5 in FIG. 4.
Figure 6:
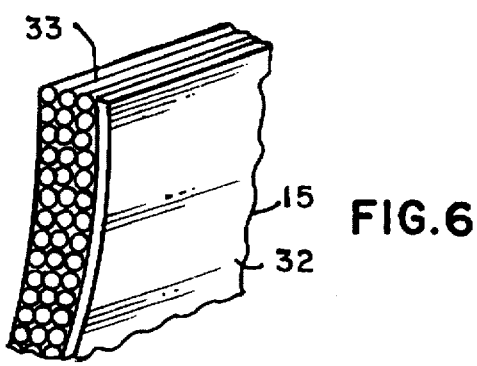
FIG. 6 is an enlarged cross-section taken along lines 6—6 in FIG. 4.

There are several methods and structures for producing integral portions of different coefficients of friction. FIGS. 5 and 6, for example, disclose portions of the balloon catheter in FIG. 4 corresponding to the first surface 27 in FIG. 5 and the second surface 32 in FIG. 6 in which the balloon 15 has a cellular or tubular honeycomb core 33. In accordance with one method, the balloon, during manufacture, is expanded in the form shown in FIGS. 3 and 4 and coated with diverse coatings over portions coextensive to the surfaces 27 and 32. The first surface 27 would be coated with a material that optimizes lubricousness while the surface 32 would be coated with a material that has a higher coefficient of friction. After the coating cures and becomes integral with the balloon 15, the balloon is collapsed and folded into the form shown in FIGS. 1 and 2. Coatings for the first surface 27 include those composed of hydrogel, silicone and hydrophilic oil materials. The second surface 32 could remain uncoated or be formed of a tacky coating, such as a polyurethane coating or even be coated with the same material as the first surface 27 that is roughened after application. Stated differently, the balloon exterior surfaces are coformed to have different coefficients of friction that permanently characterize the friction of the different surfaces.

Figure 7:
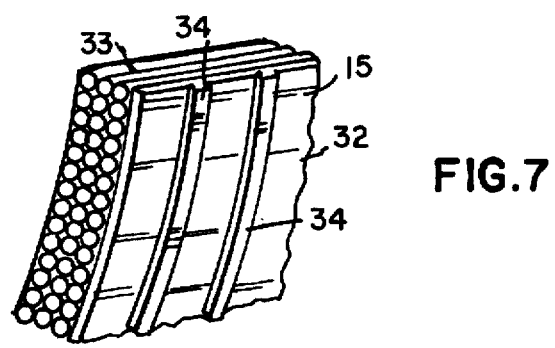
FIG. 7 depicts an alternate embodiment of the structure shown in FIG. 6.

FIG. 7 shows another embodiment of a balloon 15 in which the surface 32 is textured by forming circumferentially extending, axially spaced ribs 34. The ribs 34 can press gently into and anchor with surrounding tissue as the balloon 15 expands. This effectively provides an overall coefficient of friction that is greater than the coefficient of friction of a smooth surface 27.

Figure 8:
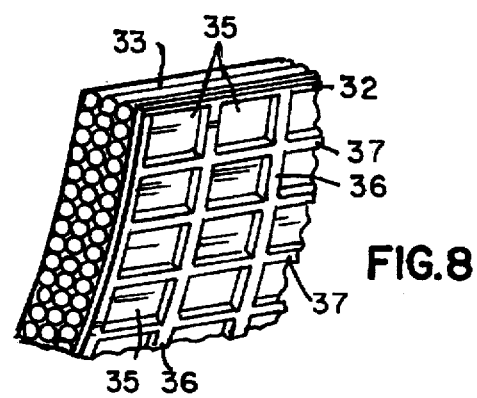
FIG. 8 shows still another alternative embodiment of the structure shown in FIG. 6.

FIG. 8 depicts another embodiment in which the surface 32 is treated with an array of molded pockets 35 bounded by circumferentially and longitudinally extending ribs 36 and 37. When expanded this waffle-like surface gently contacts adjacent tissue and anchors the balloon 15 in place. In either of the embodiments of FIGS. 7 or 8, the material forming the surfaces 32 and 27 may be the same. The ribs 34 in FIG. 7 and the ribs 36 and 37 in FIG. 8 would be coextensive only with the surface 32. In accordance with one manufacturing process, a slippery coating, such as a hydrogel material, would be applied to the entire surface of the balloon. Then a material etching process, such as laser etching, would form the ribs 34 or ribs 36 and 37 by removing the intermediate portions of the coating.

FIGS. 9 through 12 depict a balloon catheter assembly 50 with an expandable balloon 51 that extends to a distal end over a guidewire 52. Spaced tubular portions 53 and 54 of the catheter 50 support the balloon 51. The catheter is generally similar to that shown in respect to FIGS. 1 through 4.

In this particular embodiment, however, the balloon 51 is compacted by pleating. More specifically, when the balloon 51 deflates, it forms into pleats, eight pleats in this example, about a central tube 56 interconnecting the tubular portions 53 and 54 and a centrally disposed marker 57. The pleats 60 through 67 shown in FIGS. 9 and 10 are laminated structures with a base film 68 and a plurality of coatings. Specifically the pleat 60 includes a central coating 60A that is at the outer surface of the compacted balloon 51 and that is coextensive longitudinally with the balloon 51. Likewise the pleats 61 through 67 have corresponding central, exteriorly exposed, longitudinal sections 61A through 67A. Each of these surface sections 60A through 67A has a low coefficient of friction. These are essentially the only surface sections that are exposed when the balloon 51 is in a compact form.

When the balloon 51 expands about the central tube 56 as shown in FIGS. 11 and 12, the pleats 60 through 67 open into a generally circular configuration, depending of course on the tissue into which the balloon 51 expands. At pleat 60, this exposes areas 60B and 60C on either side of the central area 60A. Similarly, areas 61B through 67B and 61C through 67C are exposed on opposite sides of the central areas 61A through 67A respectively. Each of the areas 60B through 67B and 60C through 67C has a higher coefficient of friction than the surfaces of coatings 60A through 67A respectively. Moreover, the total area of the areas 60B through 67B and 60C through 67C exceeds the total area of the areas 60A through 67A.

In FIG. 12, radial lines, such as radial line 70, depict the boundary between areas such as areas 61B and 62C. In actual practice the areas 61B and 62C would be formed as a continuous coating. The radial line 70 and other similar radial lines are shown for purposes of description only.

As will be apparent, surface treatment as shown and described with FIGS. 7 and 8 can be used in the surfaces 60B through 67B to achieve angularly spaced surface portions of a greater coefficient of friction. Moreover, the embodiment shown in FIGS. 9 through 12, like the embodiment shown in FIGS. 1 through 4, provides a balloon catheter that has different coefficients of friction in its compact and expanded forms. Thus, like the embodiment of FIGS. 1 through 4, the embodiment in FIGS. 9 through 12 facilitates its placement at a lesion. Further, this embodiment also retains its position during inflation because its overall coefficient of friction increases during inflation. This embodiment differs from that shown in FIGS. 1 through 4 because in FIGS. 9 through 12 the balloon has plural surfaces of differing coefficients of friction rather than one area of each coefficient of friction.

In another specific embodiment, an uncoated balloon 15 as shown in FIG. 1 is folded into the form shown in FIG. 2, albeit more compactly form. An integral coating then is applied to the balloon 15 in a conventional manner as described, for example, in U.S. Pat. No. 5,091,205 issued Feb. 25, 1992 describing hydrophilic lubricous coatings. The entire exterior surface 27 of the balloon 15 is coated when the balloon 15 is compacted as shown in FIG. 2. When the balloon 15 expands to the form shown in FIG. 3, the coating remains limited to the surface 27. The surface 32 remains uncoated and provides a surface of greater friction.

In each of the specifically disclosed embodiments and in other evident variations a balloon catheter in its compact or deflated form produces a balloon configuration with a low coefficient of friction during the transfer of the balloon to and across a lesion. When the balloon expands, it produces at least one section having a surface with a higher coefficient of friction that dominates and increases the overall coefficient of friction for the balloon because this surface is greater than the surface exposed when the balloon is uninflated. This stabilizes the balloon in a lesion and minimizes the chances for its unwanted longitudinal displacement.

This invention has been disclosed in terms of certain embodiments. It will be apparent that many modifications, particularly in the form of different coatings and surface treatments can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. In a balloon catheter for insertion in a patient's vessel including a catheter having a lumen therethrough and an axially extending balloon formed of a layer of material that defines internal and external surfaces and disposed concentrically about one end of the catheter, said balloon communicating with the lumen to enable inflation of said balloon from a compact to an expanded configuration by the introduction of a fluid through the lumen to said balloon, the improvement comprising the division of said external surface into a plurality of first and second external angularly spaced, axially extending surface portions, said balloon, in its compact configuration, being folded to expose essentially only said first external surface portions and, in its expanded configuration, to expose both said first and second external surface portions, each of said first external surface portions being coformed with said balloon to have a first permanent characteristic of sliding friction and each of said second external surface portions being coformed with said balloon to have a second and greater permanent characteristic of sliding friction whereby the first permanent characteristic of sliding friction is determinative of the characteristic of sliding friction of said balloon in its compact configuration and the second permanent characteristic of sliding friction is substantially determinative of the overall frictional characteristic of sliding friction of said balloon in its expanded configuration.

2. A balloon catheter as recited in claim 1 wherein said balloon, in its compact configuration, has first and second folds for defining the angular extent of each of said first and second permanent external surface portions and for positioning the second permanent external surface portions inwardly of said first permanent external surface portions when said balloon is in its compact configuration.

3. A balloon catheter as recited in claim 2 wherein said first external surface portions are coformed with smooth permanent surfaces and said second external surface portions are coformed with textured permanent surfaces.

4. A balloon catheter as recited in claim 3 wherein each of said second external surface portions is coformed with permanent, axially spaced, circumferentially extending ribs.

5. A balloon catheter as recited in claim 4 wherein each of said second external surface portions additionally includes axially extending, circumferentially spaced ribs.

6. A balloon catheter as recited in claim 2 wherein each of said second external surface portions has a permanent coating with a characteristic of sliding friction that is different from the characteristic of sliding friction for each of said first external surface portions.

7. A balloon catheter as recited in claim 6 wherein said permanent coating on each of said first external surface portions produces a surface having a characteristic of sliding friction that is less than the characteristic of sliding friction produced by the permanent coating on each said second external surface portions.

8. In a balloon catheter for insertion in a patient's vessels including a catheter having a lumen therein and a balloon mounted thereon in communication with the lumen for selective inflation of said balloon from a compact form to an expanded form about an axis, the improvement of a balloon having interior and exterior surfaces, said external surface comprising first and second axially extending, angularly displaced surface portions coformed with said balloon, a first surface portion being exposed in the compact and expanded forms of said balloon and said second surface portion being exposed during expansion of said balloon from its compact form, said first and second surface portions being formed with different permanent characteristics of sliding friction whereby the first external surface portion characteristic of sliding friction is determinative of the overall characteristics of sliding friction of said balloon upon engagement with a patient's vessels and the second external surface portion characteristic of sliding friction is substantially determinative of the overall characteristic of sliding friction with respect to a patient's vessels after said balloon shifts from its compact form to its expanded form.

9. A balloon catheter as recited in claim 8 wherein one of said first and second external surface portions is formed with spaced ribs that extend circumferentially about the axis thereby to produce an external ribbed surface portion with a greater characteristic of sliding friction than the other of said external surface portions.

10. A balloon catheter as recited in claim 9 wherein said ribbed surface portion additionally includes spaced ribs that extend parallel to the axis and intersect said circumferentially extending ribs.

11. A balloon catheter as recited in claim 8 wherein one of said first and second balloon external surface portions comprises a permanent coating having a first characteristic of sliding friction that is different from the characteristic of sliding friction for the other of said external surface portions upon engagement with the patient's vessels.

12. A balloon catheter as recited in claim 11 wherein the other of said first and second external surface portions includes another permanent coating having a characteristic of sliding friction that differs from a characteristic of sliding friction for the first coating.

13. A balloon catheter as recited in claim 8 wherein one of said first and second external surface portions is textured to have a greater frictional characteristic upon engagement with the patient's vessel than the other of said first and second external surface portions.

14. A balloon catheter for percutaneous insertion through the vessels of a patient comprising:

A. a catheter having a proximal and distal end and a lumen extending between the proximal and distal ends, B. an expansible balloon at the distal end of said catheter, said balloon being selectively inflatable from a compact form to an expanded form about an axis, said balloon having an exterior surface with at least one axially extending integral surface portion coformed with a first permanent frictional characteristic that engages the patient's vessels in said compact condition and at least one other axially extending integral surface portion that exhibits a greater permanent frictional characteristic upon engagement with the patient's vessels, all of said surface portions being exposed in the expanded condition of said balloon whereby said balloon in its expanded state exhibits greater friction in contact with a patient's vessels than when the balloon in its compact state; and C. expansion means associated with said catheter lumen inflating said balloon into its expanded condition.

15. A balloon catheter as recited in claim 14 wherein said other surface portion are enfolded into the balloon in the compact condition.

16. A balloon catheter for insertion in a patient's vessels comprising:

A. a catheter having a lumen therein, and

B. an expansible balloon operatively connected with said lumen for selective inflation from a compact to an expanded condition, said balloon operatively carried on said catheter with a first integral exterior surface portion of said balloon exposed in the compact condition and a second integral exterior surface portion and said first integral surface portion being exposed upon inflation of said balloon, said first exterior surface having a first permanent frictional characteristic and said second exterior surface having a second permanent frictional characteristic that is greater than the first permanent frictional characteristic whereby the overall friction produced in the expanded state of said balloon fixes the position of said balloon in the patient's vessel and the overall friction produced in the compacted state facilitates the transfer of said balloon through the patient's vessels.

17. A balloon catheter as recited in claim 16 wherein said second exterior surface portion is formed with permanently affixed gripping means for inhibiting movement of said balloon upon inflation of said balloon.

* * * * *